(12) United States Patent
Ariav et al.

(10) Patent No.: US 7,866,212 B2
(45) Date of Patent: Jan. 11, 2011

(54) HIGH-SENSITIVITY SENSORS FOR SENSING VARIOUS PHYSIOLOGICAL PHENOMENA, PARTICULARLY USEFUL IN ANTI-SNORING APPARATUS AND METHODS

(75) Inventors: Arie Ariav, Doar-Na Hof Ashkelon (IL); Vladimir Ravitch, Ashkelon (IL); David Nitsan, Tel-Aviv (IL); Guy Meger, Haifa (IL)

(73) Assignee: Nexense Ltd., Yavne (IL)

( * ) Notice: Subject to any disclaimer, the term of this patent is extended or adjusted under 35 U.S.C. 154(b) by 960 days.

(21) Appl. No.: 11/629,183

(22) PCT Filed: Jun. 9, 2005

(86) PCT No.: PCT/IL2005/000617
§ 371 (c)(1),
(2), (4) Date: Dec. 11, 2006

(87) PCT Pub. No.: WO2005/120167
PCT Pub. Date: Dec. 22, 2005

(65) Prior Publication Data
US 2008/0306396 A1    Dec. 11, 2008

(30) Foreign Application Priority Data

| Jun. 10, 2004 | (IL) | ................................. 162472 |
| Jul. 8, 2004 | (IL) | ................................. 162939 |
| Nov. 2, 2004 | (IL) | ................................. 164991 |

(51) Int. Cl.
*G01N 29/00* (2006.01)
*A61B 5/08* (2006.01)

(52) U.S. Cl. ............................ 73/596; 73/597; 600/534

(58) Field of Classification Search .................. 73/596, 73/597, 602; 381/116, 71.11; 600/529, 586, 600/587, 546, 559, 534
See application file for complete search history.

(56) References Cited

U.S. PATENT DOCUMENTS

| 4,941,478 A | * | 7/1990 | Takeuchi et al. ............. 128/848 |
| 5,203,343 A | * | 4/1993 | Axe et al. .................... 600/538 |
| 5,458,105 A | * | 10/1995 | Taylor et al. ................. 128/848 |
| 5,503,146 A | * | 4/1996 | Froehlich et al. ........ 128/204.23 |
| 5,684,460 A | * | 11/1997 | Scanlon .................... 340/573.1 |
| 5,844,996 A | | 12/1998 | Enzmann et al. |
| 5,979,456 A | * | 11/1999 | Magovern .................... 128/899 |
| 5,987,983 A | * | 11/1999 | Ariav et al. .................... 73/488 |
| 6,491,647 B1 | | 12/2002 | Bridger et al. |
| 6,551,256 B1 | * | 4/2003 | Stasz et al. .................. 600/586 |
| 6,621,278 B2 | | 9/2003 | Ariav |
| 6,716,169 B2 | | 4/2004 | Muramatsu et al. |
| 6,935,335 B1 | * | 8/2005 | Lehrman et al. ........ 128/200.24 |
| 6,984,207 B1 | | 1/2006 | Sullivan et al. |
| 7,320,320 B2 | * | 1/2008 | Berthon-Jones ........ 128/204.23 |

* cited by examiner

*Primary Examiner*—J M Saint Surin

(57) ABSTRACT

A mechanical vibration sensor adapted to be brought into contact with an object for sensing mechanical vibrations in the object, includes a body of a soft elastomeric material having high transmissivity and low attenuation properties with respect to a preselected type of energy waves; and a pair of transducers mounted, by mounting members having high attenuation properties with respect to the energy waves, in spaced relationship to each other to define a transmission channel between the transducers. Such sensor is particularly useful in a method and apparatus for controlling snoring by a person, by utilizing a stimulus device effective, when sensing snoring, to immediately produce a response in the person tending to interrupt the person's snoring.

10 Claims, 10 Drawing Sheets

HIGH-SENSITIVITY SENSORS FOR SENSING VARIOUS PHYSIOLOGICAL PHENOMENA, PARTICULARLY USEFUL IN ANTI-SNORING APPARATUS AND METHODS

RELATED APPLICATIONS

This Application is a National Phase of PCT Patent Application No. PCT/IL2005/000617 having International Filing Date of Jun. 9, 2005, which claims the benefit of Israel Patent Application Nos. 164991 filed on Nov. 2, 2004, 162939 filed Jul. 8, 2004, and 162472 filed Jun. 10, 2004. The contents of the above Applications are all incorporated herein by reference.

FIELD AND BACKGROUND OF THE INVENTION

The present invention relates to high-sensitivity sensors for sensing various physiological phenomena, such as respiratory activity, cardiac activity, body movements, sleeping activity, etc. The invention is particularly useful in sensing snoring, and is therefore described below as one of the preferred embodiments in a method and apparatus for detecting snoring and for actuating a stimulus device to produce a feedback response tending to reduce or eliminate the snoring.

The preferred embodiments of the invention described below utilize the type of sensors described in International Patent Application No. PCT/IL2004/000138, filed Feb. 12, 2004, and U.S. Pat. No. 6,621,278, the contents of which are incorporated herein by reference. It will be appreciated, however, that while such sensors are preferred, other types of sensors may also be used as described more particularly below.

The above-cited International Patent Application and U.S. patent describe sensors for sensing, with extremely high sensitivity, various parameters having a known or determinable relationship with respect to the transit time of an energy wave (e.g., electromagnetic, acoustic) through a medium (solid, liquid or gas). Briefly, this is done by transmitting a cyclically-repeating energy wave through a transmission channel in the medium; continuously changing the frequency of the transmission according to changes in the sensed parameter while maintaining the number of waves in a loop including the transmission channel as a whole integer; and utilizing the changes in frequency in the transmission channel to provide a continuous indication of the sensed parameter. Thus, a change in the sensed parameter changes the transit distance and/or the transit velocity, and thereby the transit time, of the energy wave through the transmission channel.

The above-cited International Patent Application discloses a sensor construction in which the medium of the transmission channel between the transmitter and receiver is a body of a soft elastomeric material having high transmissivity and low attenuation properties with respect to the transmitted energy waves. Such sensors are particularly useful as mechanical vibration sensors, both the displacement type and the acceleration type, which are to be brought into contact with an object for sensing mechanical vibrations in the object.

As will be described below, the present invention provides novel constructions of such mechanical vibration sensors which make them particularly useful for monitoring various physiological phenomena, including vital signs, e.g. respiratory activity (breathing), cardiac activity (heartbeat), and body movements. Potential applications of the present invention include apnea monitors, elderly are monitors, asthma attack monitors, and sleep-condition monitors. Examples of the latter application include devices to actuate an alarm in case an alarm condition is detected, to detect sleep disorders, to control a wake-up alarm for comfortable awakening, and to reduce or eliminate snoring.

The invention is particularly useful for detecting sleep disorders and for controlling a wake-up alarm since it efficiently senses various body activities, such as respiration rate, pulse rate, and body motions helpful in identifying a sleep disorder or comfortable wake-up time, e.g., as described in U.S. Pat. Nos. 5,101,831, 6,752,766 and 6,856,829, the contents of which are incorporated herein by reference.

The invention is also especially useful to reduce or eliminate snoring. Thus, it is generally recognized that snoring not only unduly disturbs those in the immediate vicinity, but probably more important, may be an indication of a serious sleep disorder which can lead to strokes, heart diseases, hypertension, etc. Many sound-type sensors have been developed for this purpose, but such sensors are also sensitive to sounds other than snoring sounds, and are therefore generally subject to a relatively high rate of false alarms.

OBJECTS AND BRIEF SUMMARY OF THE PRESENT INVENTION

One object of the present invention is to provide improvements particularly (but not exclusively) in the mechanical vibration sensors and apparatus described in the above-cited International Patent Application for purposes of decreasing the noise and for increasing the stability of the sensor output. Another object of the present invention is to provide a method and apparatus for detecting a number of sleep disorders, and particularly reducing or eliminating snoring.

According to one aspect of the present invention, there is provided a mechanical vibration sensor adapted to be brought into contact with an object for sensing mechanical vibrations in the object, comprising: a body of a soft elastomeric material having high transmissivity and low attenuation properties with respect to a preselected type of energy waves; and a pair of transducers mounted in spaced relationship to each other in the body of soft elastomeric material to define a transmission channel between them, with one transducer acting as a transmitter of the energy waves and the other transducer acting as a receiver of the energy waves; the body of soft elastomeric material having a face adapted to be brought into contact with the object such that the mechanical vibrations in the object are sensed by the changes produced thereby in the transit time of the energy waves through the transmission channel; characterized in that each of the transducers is mounted in the spaced relation to each other in the body of soft elastomeric material by a mounting member having high attenuation properties with respect to the energy waves.

As indicated earlier, such mechanical vibration sensors may be of the displacement type which sense displacements, or of the acceleration-type which sense a rate of change of displacement.

In the described preferred embodiments, the energy waves are acoustic waves, and the material of high attenuation properties used for the mounting members is a natural or synthetic rubber, whereas the body of soft elastomeric material defining the transmission channel between the transmitter and receiver is a silicon or polyurethane elastomer.

In the described preferred embodiments, the sensor assembly senses various body activities of the user. For example, the processor may be designed or programmed to permit analysis of data recorded during a sleep session for identifying the occurrence, of one or more of the following body activities: respiration activity; heart beat; REM (rapid eye-movement)

sleeping; non-REM sleeping; restlessness, including restless leg syndrome (RLS); apnea; asthma attack; epileptic attack; snoring; teeth grinding; and nightmarish behavior. Monitoring and recording the foregoing body activities may be used for one or more of the following purposes: to actuate an alarm should an emergency condition arise; to detect various types of sleep disorders; to control a wake-up alarm in order to better assure more comfortable awakening; and/or to reduce or eliminate snoring.

As indicated above, the described apparatus is particularly useful for reducing or eliminating snoring or other predetermined body condition. Therefore, according to another aspect of the present invention, there is provided apparatus (and also a method) for controlling snoring or other body condition by a person, comprising: a sensor for sensing the predetermined body condition of the person while sleeping, and for outputting a sensor signal corresponding to the sensed body condition; a stimulus device effective, when actuated, to immediately produce a response in the person tending to interrupt the sensed body condition; and a processor for processing said outputted sensor signal to determine whether it indicates the presence of the sensed body condition, and if so, for actuating said stimulus device to produce the response tending to interrupt the sensed body condition; characterized in that said sensor is a mechanical vibrations sensor and is included between, and in contact with, a pair of plates of larger size than said sensor for sensing mechanical vibrations in an external part of the person's body and for transmitting said mechanical vibrations to said sensor for generating and outputting said sensor signal. Using such a mechanical vibrations sensor, rather than an acoustic sensor, thus avoids many of the disadvantages of acoustical sensors, as well as enables the apparatus to be used for performing many other functions, as will be discussed more particularly below.

Further features and advantages of the invention will be apparent from the description below.

BRIEF DESCRIPTION OF THE DRAWINGS

The invention is herein described, by way of example only, with reference to the accompanying drawings, wherein.

Figure 1:
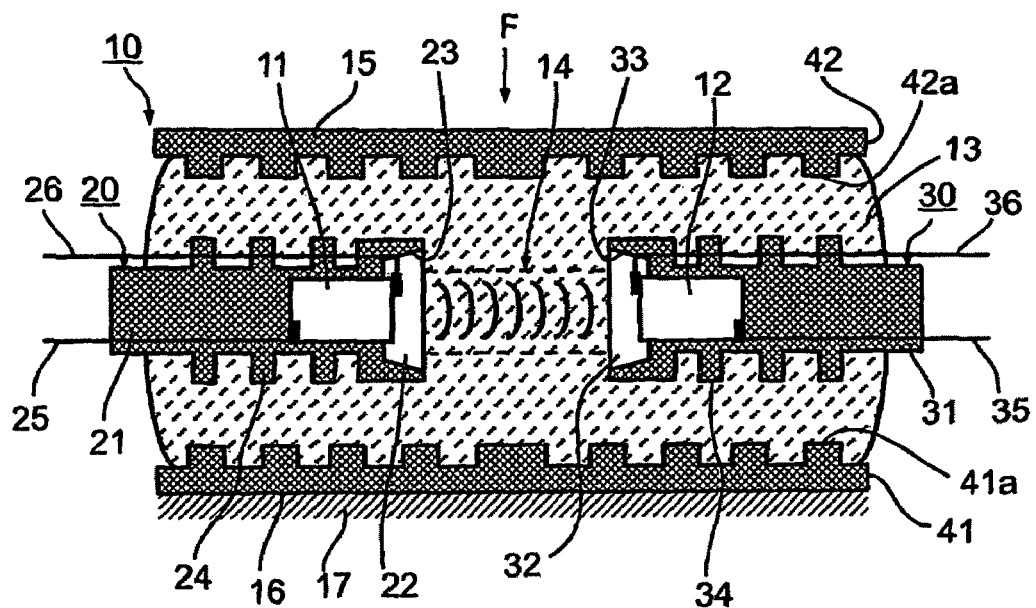
FIG. 1 is a longitudinal sectional view illustrating one form of sensor constructed in accordance with the present invention.

It is to be understood that the foregoing drawings, and the description below, are provided primarily for purposes of facilitating understanding the conceptual aspects of the invention and possible embodiments thereof including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

As indicated above, the sensors illustrated in the drawings are based on the sensor constructions described in the above-cited PCT Application. That application described many sensor constructions which included a body of a soft elastomeric material defining a transmission channel for acoustic energy waves transmitted by a transmitter to a receiver such that monitoring the transit time of such energy waves through the transmission channel enabled sensing any one of a number of parameters or conditions having a known or determinable influence on such transit time. The present invention is particularly (but not exclusively) useful in such sensor constructions for purposes of monitoring mechanical vibrations in an object contacted by the sensor, while decreasing the noise and/or increasing the stability of the sensor output. As will be more particularly described below, such a sensor is particularly useful for monitoring various physiological phenomena while the subject is sleeping in order to monitor heart and respiration activity, to detect various sleep disorders, to control a wakeup alarm for more comfortable awakening, to reduce or eliminate snoring, etc.

Figure 2:
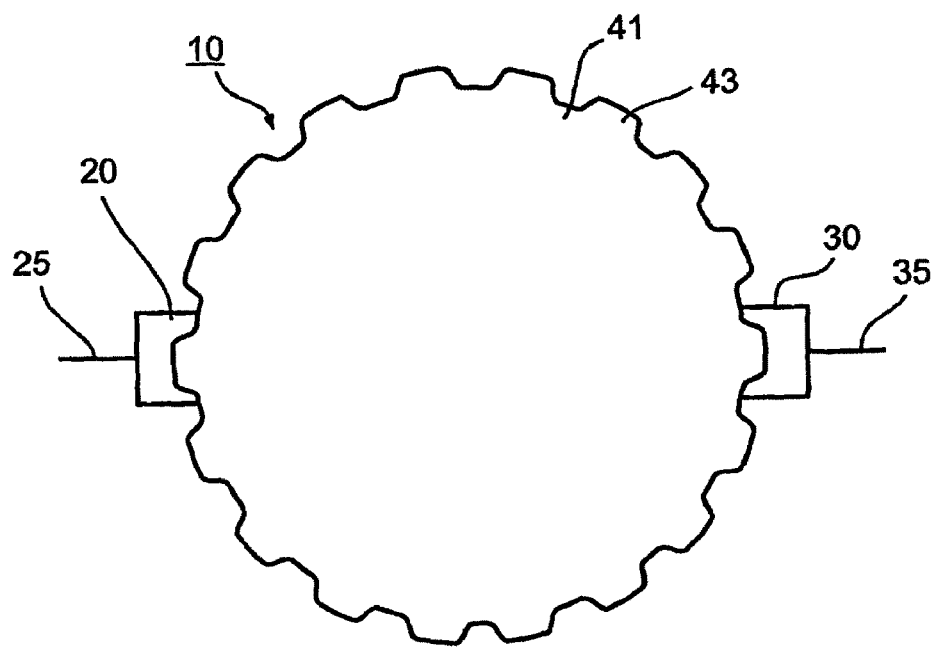
FIG. 2 is a top plan view of the sensor of FIG. 1.

The sensor illustrated in FIGS. 1 and 2, therein generally designated 10, includes an acoustic transmitter transducer 11 and an acoustic receiver transducer 12 embedded in spaced relationship to each other within a body 13 of a soft elastomeric material. The portion of body 13 between transmitter 11 and receiver 12 thus defines a transmission channel 14 for the energy waves transmitted by the transmitter to the receiver. In this case, the transmitter and receiver transmit and receive acoustic waves, such that the transmission channel 14 between them is an acoustic transmission channel.

One face 15 of sensor 10 is exposed to the parameter to be sensed or measured, e.g., force, pressure, vibrations, etc., as indicated by arrow F. The opposite face 16 of sensor 10 is restrained against movement, for example by being mounted on a rigid backing member 17, such that force F applied to face 15 will displace transmitter 11 and receiver 12 further apart from each other in accordance with the magnitude of the applied force. Sensor 10 is thus a displacement-type sensor, in that sensing the displacement or relative position of receiver 12 with respect to transmitter 11 enables precise sensing of the force F.

According to one feature of the present invention, the transmitter 11 and receiver 12 are mounted within body 13 of soft elastomeric material by mounting members 20, 30 of a material having high attenuation properties with respect to the energy waves. Each mounting member 20, 30 is of a configuration to substantially enclose its respective transmitter 11 or receiver 12, except for the side facing the transmission channel 14.

Thus, as shown particularly in FIG. 1, each of the two mounting members 20, 30, is a preformed member, e.g., produced by injection molding. Each includes a cylindrical portion 21, 31 distal from the transmission channel 14, and an open cavity 22, 32 proximal to the transmission channel 14 for receiving the transmitter 11 and receiver 12, respectively. Transmitter 11 and receiver 12 are each received within the cavity of its respective mounting member 20, 30 so as to be spaced slightly inwardly of the respective mounting member; that is, the cavity of each mounting member extends past its respective transmitter/receiver towards transmission channel 14. Each cavity is formed with outer diverging surfaces, as shown at 23 and 33, respectively, diverging in the direction towards the transmission channel, such as to focus the energy waves transmitted by the transmitter 11 towards the transmission channel 14, and to focus the energy waves received by the receiver 12 from the transmission channel 14.

While each mounting member 20, 30 is of circular cross-section, the portion of each cavity 22, 23 receiving the transmitter 11 or receiver 12 is preferably of the same cross-section as its respective transmitter or receiver so as to receive it with a snug fit. The outer diverging surfaces 23, 33 are preferably of a conical configuration.

As further seen in FIG. 1, the outer surface of the mounting members 20, 30 is formed with annular ribs, as shown at 24, 34, respectively. Such a construction, among other advantages to be described below, better anchors the mounting members and their respective transmitter 11 and receiver 12 within body 13 of soft elastomeric material.

The electrical wire connections 25, 26 for the transmitter 11, and 35, 36 for the receiver 12, are preferably passed through small openings in the respective mounting member 20, 30. Thus, as seen in FIG. 1, electrical connecting wires 25, 35, connected to one side of the transmitter 11 and receiver 12, respectively, are each passed through an opening in the cylindrical portion 21, 31 of the respective mounting member 20, 30; whereas electrical connecting wires 26, 36, connected to the other side of the transmitter 11 and receiver 12, respectively, are each passed through the ribs 24, 34 of the respective mounting member. The openings for accommodating the electrical connecting wires should be as small as possible. They may be formed, for example, by piercing the respective mounting member by a sharpened wire, tool or the like, after the mounting member has been injection molded.

As one way of making the illustrated sensor, the two mounting members 20, 30, together with the transmitter 11 mounted in the cavity of one and the receiver 12 mounted in the cavity of the other, may be disposed in a mold; and the mold may then be filled with the soft elastomeric material defining body 13 so as to embed the mounting members and their respective transmitter and receiver in the soft elastomeric material with the transmission channel 14 between them.

Before the body of soft elastomeric material 13 is applied to the mold, the bottom of the mold is preferably lined with a preformed layer 41 of a material having high attenuation properties with respect to the energy waves transmitted by the transmitter 11. The upper surface of layer 41 is pre-formed with ribs as shown at 41a, such that when the soft elastomeric material defining body 13 is introduced into the mold, the body of soft elastomeric material becomes complementarily ribbed as shown in FIG. 1.

After the soft elastomeric material defining body 13 has been poured into the mold, another preformed layer 42 of a material having high attenuation properties is applied to the upper surface of the elastomeric material. Layer 42 is also pre-formed with ribs on its inner surface, as shown at 42a, FIG. 1, so that the surface of the elastomeric material contacting layer 42 also becomes complementarily ribbed.

The mold is of generally cylindrical configuration such that the molded elastomeric body 13 (including the mounting members 20, 30, the transmitter 11, the receiver 12 and the two outer layers 41, 42 embedded therein) produced by the mold is also of generally cylindrical configuration. However, the circumferential surface of the mold is preferably formed with a plurality of axially-extending, circumferentially-spaced ribs, as shown in the plan view of FIG. 2, such that the circumferential surface of the cylindrical composite body produced by the mold is also formed with a plurality of axially-extending, circumferentially-spaced ribs 43.

It will thus be seen that in the sensor illustrated in FIGS. 1 and 2, the body of soft elastomeric material 13 define, between transmitter 11 and receiver 12, an acoustic channel 14 of soft elastomeric material having high transmissivity and low attenuation properties with respect to the acoustic energy waves transmitted by the transmitter. It will also be seen that the mounting members 20, 30, being of a material having high attenuation properties with respect to the transmitted acoustic energy waves, tend to absorb all the acoustic waves except those in the transmission channel 14. It will further be seen that the diverging surfaces 23, 33 in the respective mounting members 20, 30, which extend forwardly of the transmitter 11 and receiver 12 mounted by these mounting members, tend to focus the energy from transmitter 11 to the transmission channel 14, and focus the energy from the transmission channel to the receiver 12.

Since the two outer layers 41, 42, are also of a material having high attenuation properties with respect to the transmitted acoustic waves, such layers further absorb the acoustic waves outside of the transmission channel 14. The dissipation of such acoustic waves outside the transmission channel, and their absorption by the outer layers 41, 42, are further enhanced by ribbed surfaces 41a, 42a of layers 41, 42; and ribs 43 (FIG. 2) in the outer cylindrical surface of elastomeric body 13. The ribbed outer surfaces of the mounting members 20, 30, together with the complementary ribbed contacting surfaces of the soft elastomeric material body 13, not only securely anchor the mounting members, and the transmitter 11 and receiver 12 mounted thereby, within body 13, but also further dissipate and absorb acoustic energy waves outside of the transmission channel 14.

As a result of the foregoing features in the construction of the sensor illustrated in FIGS. 1 and 2, the illustrated sensor is capable of sensing mechanical vibrations in an object contacting face 15 of the sensor while substantially reducing noise and increasing stability in the sensor output.

Figure 3:
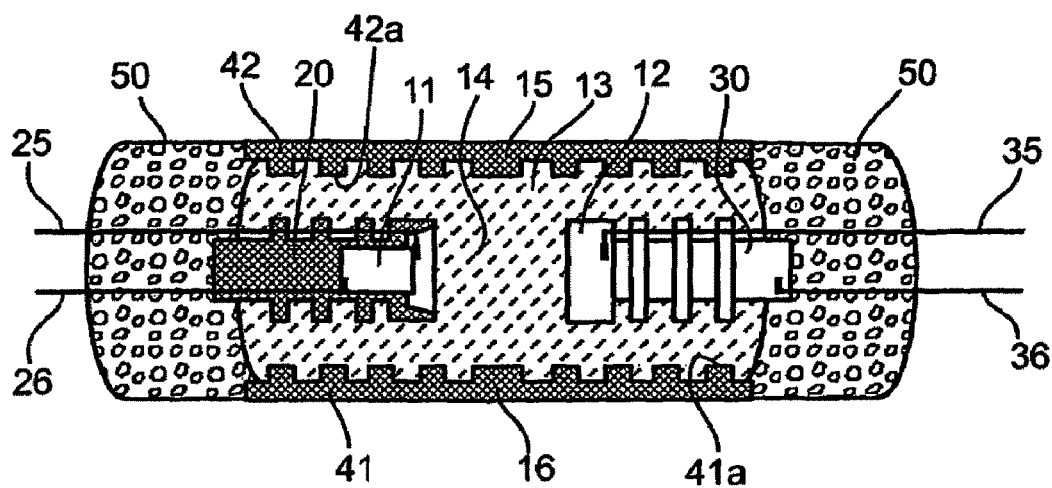
FIGS. 3 and 4 are views, corresponding to those of FIGS. 1 and 2, respectively, but illustrating a modification in the sensor of FIGS. 1 and 2.
Figure 4:
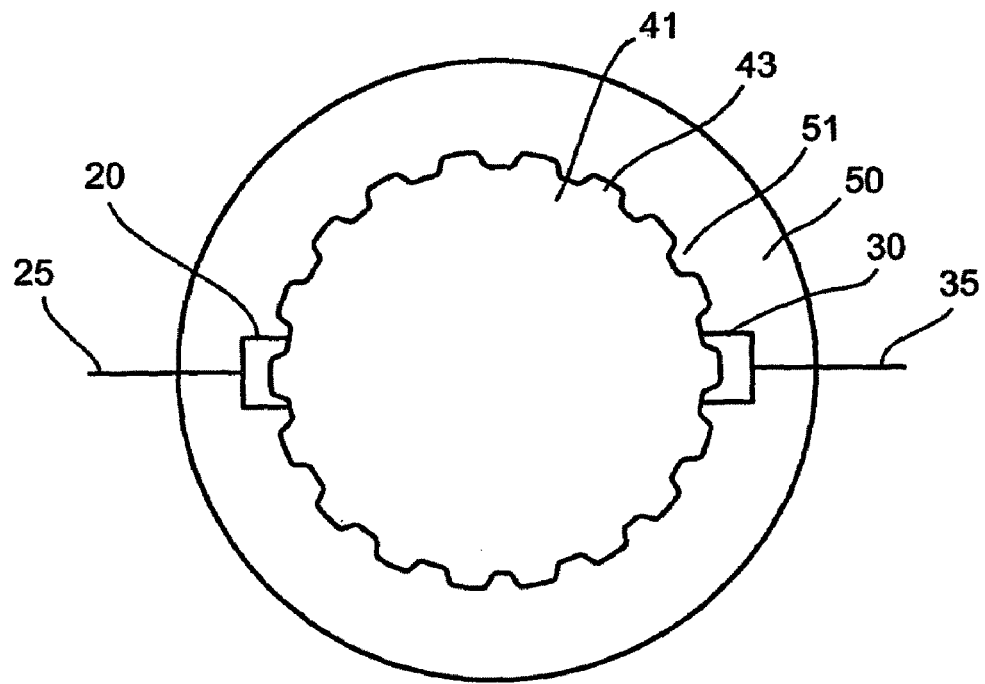

FIGS. 3 and 4 illustrate a sensor of the same construction as that illustrated in FIGS. 1 and 2, but provided with an outer annular body 50 enclosing and contacting the outer surface of the soft elastomeric body 13. Outer annular body 50 is of a material having high attenuation properties and is preferably sponged so as to be softer than elastomeric body 13. Annular body 50 is preferably molded around elastomeric body 13 so that it will also produce axially-extending circumferentially-spaced ribs, as shown at 51, complementary to the ribs 43 formed in the elastomeric body 13. Annular body 50 and its ribs 51 further attenuate the unwanted acoustic signals, i.e., all the acoustic signals except those in the transmission channel 14 between transmitter 11 and receiver 12.

For purposes of example, body 13 of soft elastomeric material, having high transmissivity and low attenuation properties with respect to acoustic waves, is preferably a silicon elastomer, such as described in the above-cited PCT Application, or a polyurethane elastomer. Preferably, the elastomer has a Shore A hardness of 7-20, most preferably about 10. On the other hand, the material having high attenuation properties with respect to acoustic waves used for the mounting members 20, 30 and the two outer layers 41, 42, is preferably a natural or synthetic rubber, somewhat harder than elastomeric body 13. Annular body 50 of FIGS. 3 and 4, if used, is preferably of a high attenuation rubber but sponged in order to make it softer than elastomeric body 13.

Figure 5:
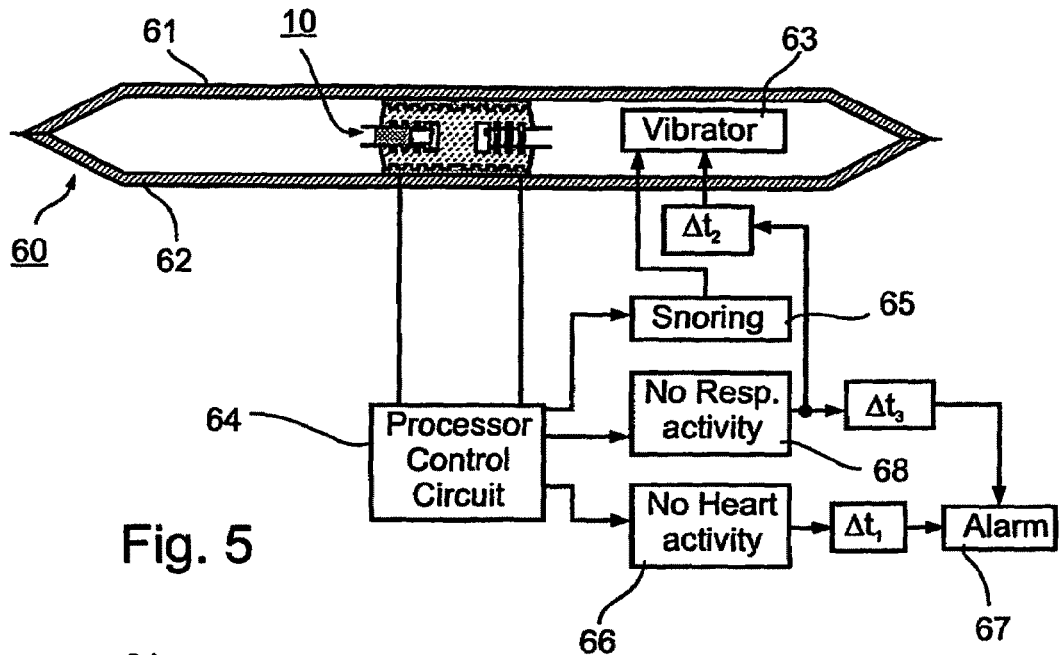
FIG. 5 is a block diagram illustrating apparatus including a sensor assembly constructed in accordance with the present invention for introduction within, over, or under, a mattress for detecting cessation of breathing, cardiac activity, snoring, etc., as described in the above-cited PCT/IL2004/000138.

FIG. 5 illustrates apparatus including a sensor assembly 60 incorporating a sensor 10 as described above mounted between and in contact with a pair of plates 61, 62, of larger size than the sensor to serve as an enclosure for the sensor. Assembly 60 illustrated in FIG. 5 is for introduction into, over, or under a mattress (or a pillow) in order to monitor respiratory activity, sleep conditions, cardiac activity, physical movements, snoring, etc. of a person occupying the mattress. The illustrated sensor assembly could also be mounted between two mattresses, e.g., an upper hard mattress and a lower soft mattress, in which case the sensor assembly would act like an acceleration-type sensor. When used for anti-snoring or wake-up purposes as described below, sensor assembly 60 also includes a vibrator 63.

The illustrated sensor apparatus further includes a processor control system 64 which produces one or more of the following outputs:

(a) A first output 65 is produced when detecting snoring by the person. This output may be used to actuate vibrator 63, or another stimulus device, effective to immediately produce a response in the person tending to interrupt the person's snoring, with the object of creating a "stimulus and response" reflex process which reduces or eliminates snoring and assures a better sleep quality.

(b) A second output 66 is produced when no heart activity is detected for a predetermined period of time ($\Delta t_1$, e.g., five seconds) to actuate an alarm 67.

(c) A third output 68 is produced when no respiratory activity is detected, which, if it lasts for a predetermined time interval ($\Delta t_2$, e.g., 10 seconds), actuates vibrator 63 in an attempt to stimulate the person; but if the lack of respiratory activity continues for an additional time interval ($\Delta t_3$, e.g., an additional 10 seconds, or 20 seconds maximum), the alarm 67 is actuated.

As described in the above-cited PCT Application, such a sensor assembly may be provided for a single person (e.g., baby, elderly patient, snorer), or for two persons, (e.g., two elderly persons or two snorers) occupying a double bed. In the latter case, one sensor could be provided for each person so as to actuate its respective stimulus device in order to reduce or eliminate snoring, or to actuate its respective alarm in order to alert the other person whenever an alarm condition is found to be present.

Figure 6:
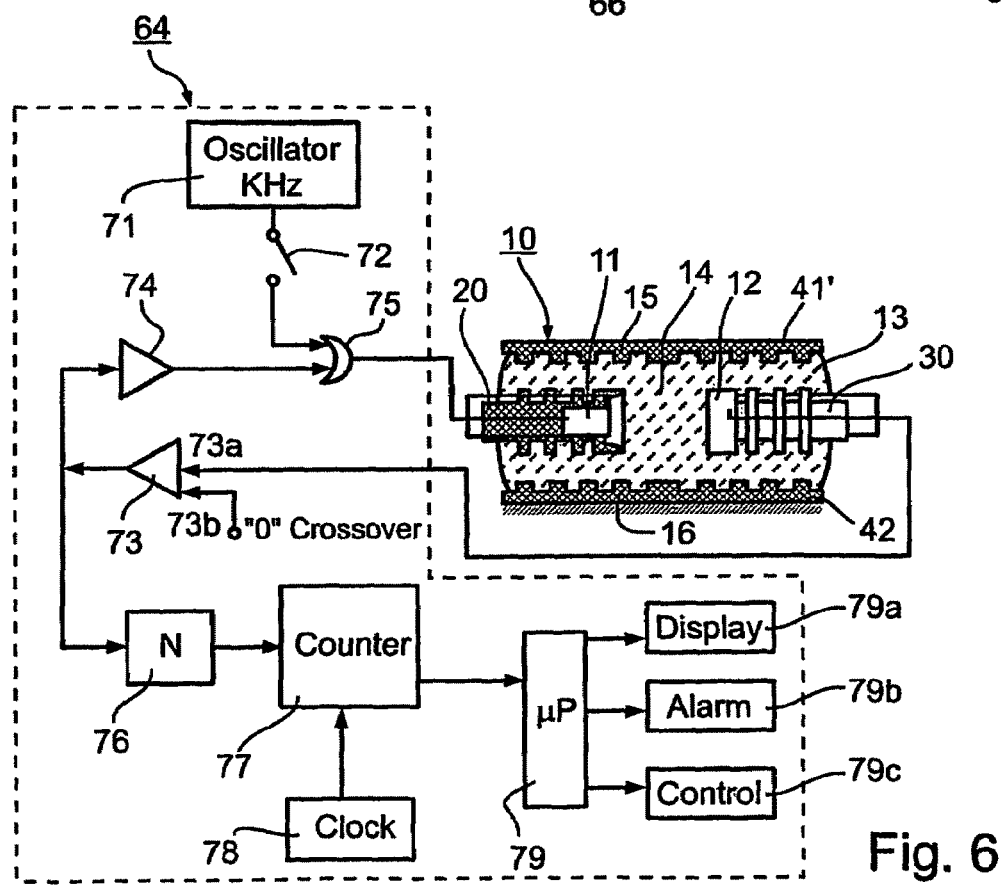
FIG. 6 is a block diagram more particularly illustrating the processor and control circuit in the apparatus of FIG. 5.

FIG. 6 more particularly describes a preferred control circuit 64 which may be used in the sensor apparatus of FIG. 5, as more particularly described in the above-cited International Patent Application.

Initially, oscillator 71 is energized while switch 72 is closed so as to cause transmitter 11 to transmit a succession of acoustic pulses until the pulses are received by receiver 12. Once the pulses are received by receiver 12, switch 72 is opened so that the pulses received by receiver 12 are thereafter used for controlling the transmitter 11.

As shown in FIG. 6, the acoustic signals received by receiver 12 are fed to a comparator 73 via its input 73a. Comparator 73 includes a second input 73b connected to a predetermined bias so as to detect a predetermined fiducial or reference point in the received signal. In the example illustrated in FIG. 6, this predetermined fiducial point is the "zero" cross-over point of the received signal; therefore, input 73b of comparator 73 is at a zero bias.

The output of comparator 73 is fed to an amplifier 74, e.g., a monostable oscillator, which is triggered to produce an output signal at each fiducial point (zero cross-over point) in the signals received by receiver 12. The outputs from amplifier 74 are fed via an OR-gate 75 to trigger the transmitter 11 for the next acoustic pulse. Since switch 72 is open, transmitter 11 will thus be triggered by each signal received by the receiver 12 to transmit the next acoustic pulse in the succession of pulses.

It will thus be seen that the frequency of the output pulses or signals from transmitter 12 will change with a change in the spacing between the transmitter 11 and receiver 12. It will also be seen that the number of wavelengths or pulses in the loop including transmitter 11 and receiver 12 will be a whole integer. This change in frequency by the transmitter 11, while maintaining the number of waves between the transmitter and receiver 12 as a whole integer, enables a precise determination to be made of the transit time in the acoustic channel, and thereby of the distance between the transmitter and receiver.

A summing circuit, including an N-counter 76, another counter 77 controlled by a clock 78, and a microprocessor 79, enables the detected frequency difference, and thereby the measurement precision, to be increased by a factor "N". Thus, the precision of the measurement can be preset, almost without limitation, by the selection of the appropriate clock rate for clock 78, and summation factor "N" for counter 77.

As further shown in FIG. 6, the output from microprocessor 79 may be used for display, alarm and/or control purposes, as schematically shown at 79a, 79b and 79c.

Further details of the construction and operation of such an apparatus are described in the above-cited International Application and U.S. Pat. No. 6,621,278, both incorporated herein by reference. For example, U.S. Pat. No. 6,621,278 includes a modulation feature, and also a delay line feature, which significantly extend the possible applications of such apparatus for measuring various types of parameters.

Figure 7:
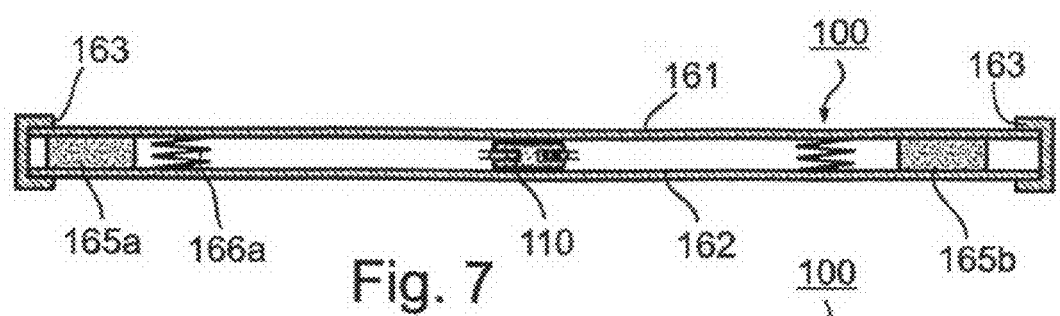
FIG. 7 is an transverse sectional view illustrating another construction of a sensor assembly in accordance with the present invention.
Figure 8:
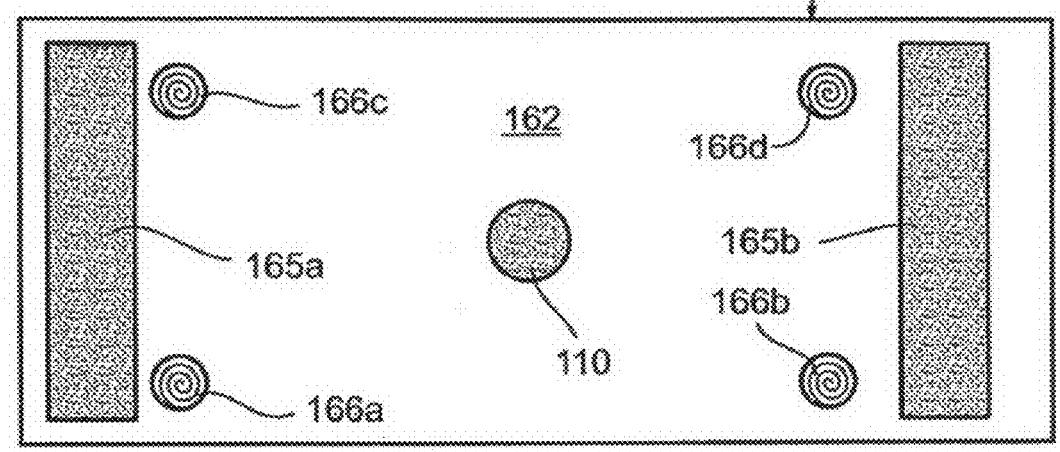
FIG. 8 is a top plan view of the sensor assembly of FIG. 7, with the rectangular frame and upper plate removed to show internal structure.

FIGS. 7 and 8 illustrate a sensor assembly generally similar to that illustrated in FIG. 5, but provided with a number of features which further decrease the noise in, and increase the stability of, the sensor output.

Thus, the sensor assembly illustrated in FIGS. 7 and 8, therein generally designated 100, includes a sensor 110 corresponding to sensor 10 described above, sandwiched between two large-sized plates 161, 162, received within a rectangular frame 163. Plates 161, 162 and frame 163 define a rectangular enclosure for sensor 110, which is located centrally of the enclosure. On each of the two opposite sides of sensor 110, the enclosure includes an elongated resilient pad 165a, 165b of soft sponge-rubber, and a pair of elastic coil springs 166a-166d between the respective sponge-rubber resilient pad and the sensor.

Frame 163 retains plates 161, 162 in contact with the opposite sides of sensor 110, the resilient pads 165a, 165b, and the coil springs 166a-166d. The resilient pads 165a, 165b are preferably of a material having high attenuation with respect to acoustic waves.

Providing the resilient pads 165a, 165b, and the elastic springs 16a-16d, in the arrangement illustrated in FIGS. 7 an 8 has been found effective to filter-out and/or to absorb environmental noises, etc, thereby making the sensor output more sensitive and more stable, particularly when placed under a mattress to monitor respiratory activity, cardiac activity, body movements, sleep states, snoring, etc, of a person occupying the mattress, as described above.

Figure 9:
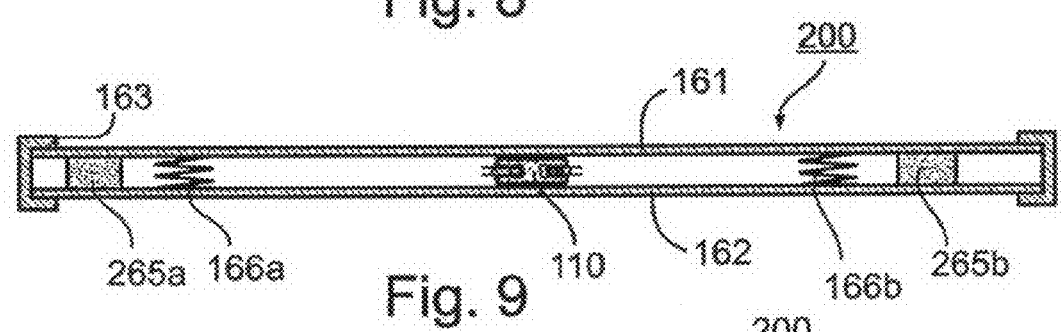
FIGS. 9 and 10 are views corresponding to those of FIGS. 7 and 8, respectively, illustrating another construction of sensor assembly in accordance with the present invention.
Figure 10:
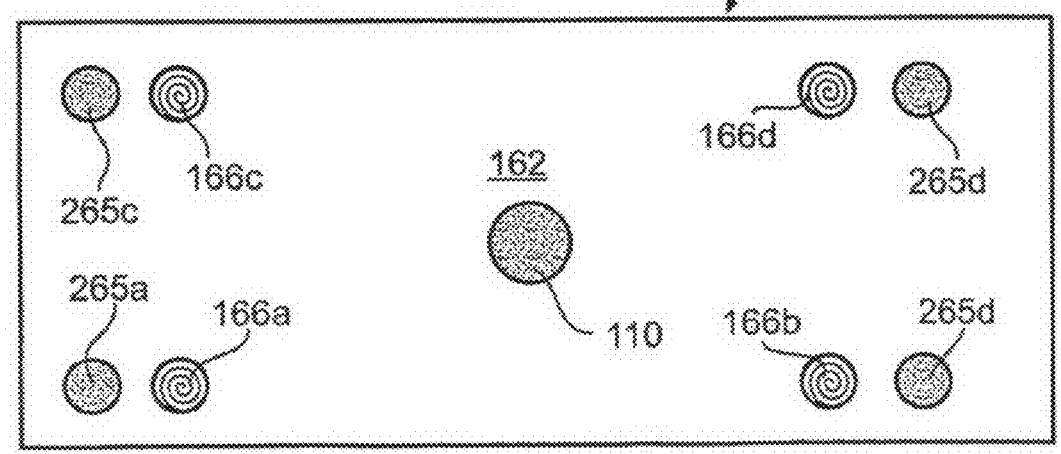

FIGS. 9 and 10 illustrate a sensor assembly 200 differing from that of FIGS. 7 and 8 mainly in the configuration and material of the resilient pads. Thus, resilient pads 165a, 165b in FIGS. 7 and 8, are replaced by four circular pads 265a-265d located at the four corners of the sensor plate assembly 200, between the respective coil spring 166a-166d and the outer periphery of that assembly. Pads 265a-265d may be of the same elastomeric material as used in sensor 110. They may be used alone without the springs 166a-166c; the springs may also be used alone without the pads to produce an accelerator-type sensor.

As a preferred construction, the material of the resilient pads 265a-265d, and also of the part of sensor 110 defining the acoustic channel between the transmitter and receiver, is preferably a silicone or polyurethane elastomer having a Shore hardness of about 10; the diameter of each such pad, as well as of the overall sensor 110 and each of the coil springs 166a-166d, is about 20 mm; the length of plates 161, 162 is about 400 mm; and the width of the plates is about 250 mm.

Figure 11:
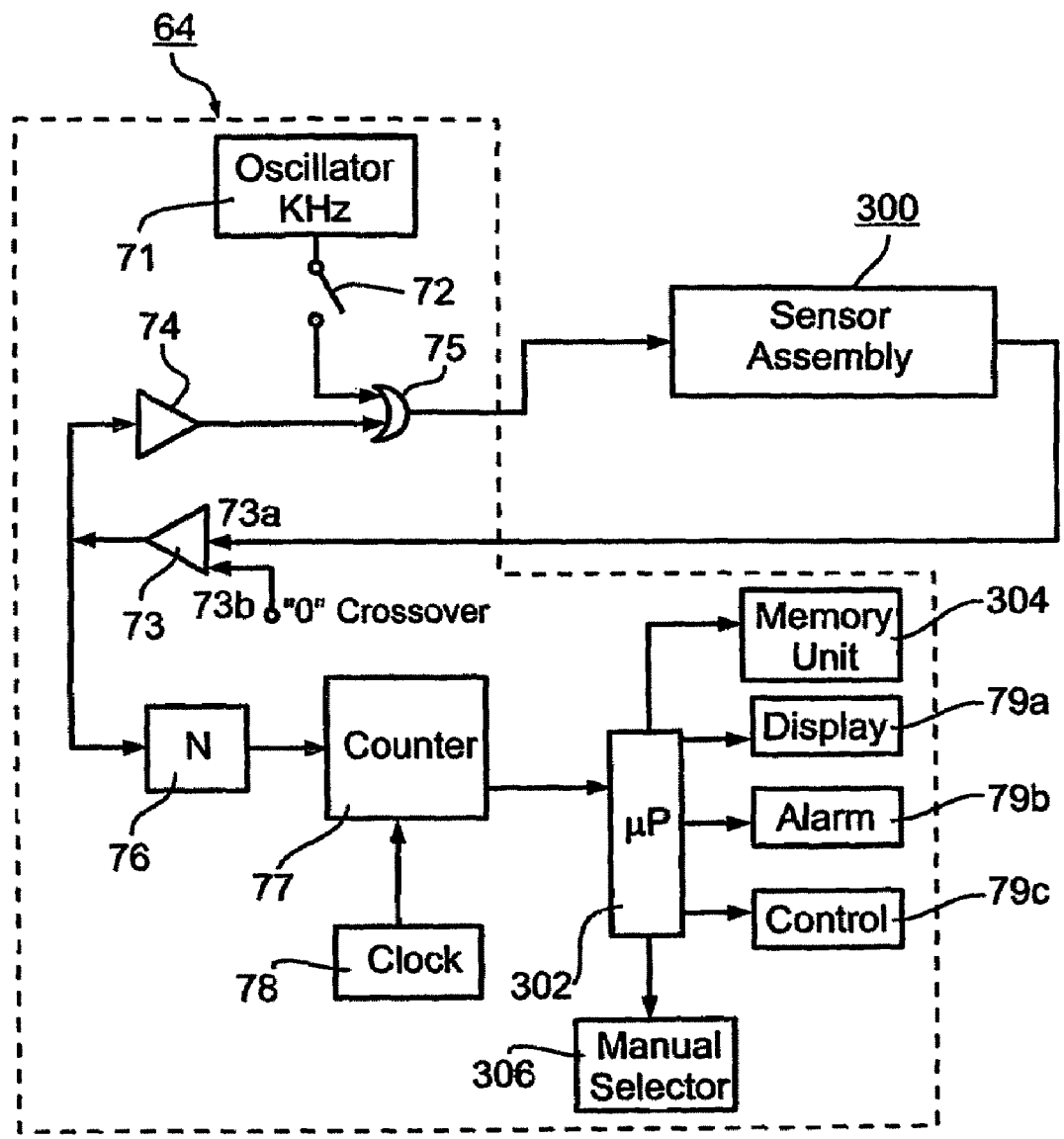
FIG. 11 is a block diagram illustrating a modification in the processor of FIG. 6.

FIG. 11 illustrates sensor apparatus similar to that of FIG. 6, but provided with additional features which extend the possible use of the apparatus for monitoring other physiological phenomena. The apparatus illustrated in FIG. 11 includes a sensor, generally designated 300, which may be of the construction illustrated in FIG. 6, or of any of the other described constructions. The FIG. 11 apparatus also includes a processor control system, which may be the same as control system 64 illustrated in FIG. 6, and therefore many components of the control system appearing in FIG. 6 are identified by the same reference numerals to facilitate understanding.

An important feature in the apparatus illustrated in FIG. 11 is that the microprocessor 302 (corresponding to microprocessor 79 in FIG. 6) is designed or programmed to perform a number of additional functions, as will be described more particularly below. In addition, the apparatus illustrated in FIG. 11 includes a memory, generally designated 304, for recording data sensed by the sensor 300 in a manner enabling convenient analysis and/or readout of the recorded data via the display 79a. Memory unit 304 is preferably a removable unit permitting it to be conveniently removed for analysis at another location, e.g., at a physician's office or medical center. In addition, the FIG. 11 apparatus also includes a manual input 306, such as a selector keyboard, knob, etc., for selecting one or more of the body activities to be detected and/or displayed, for controlling the resolution of the apparatus, etc.

Thus, the sensor apparatus illustrated in FIG. 11 is capable of sensing a large number of body activities of a user in addition to respiration and heart beat. For example, if the sensor assembly 300 is operatively coupled to a user, e.g., by direct contact or via a mattress, the illustrated apparatus is capable of sensing a large number of body activities, in addition to respiration and heart beat, including: REM sleeping; non-REM sleeping; restlessness before, during, or after sleeping; apnea; asthma attack; epileptic attack; snoring; teeth grinding; nightmarish behavior, etc. Microprocessor 302 would be programmed to enable detection of one or more of the above body activities, and to produce the appropriate read out in the display 79a, to actuate the alarm 79b, or to actuate another control device (e.g., a vibrator, 63, FIG. 5), when appropriate, for anti-snoring or wake-up purposes, as described below.

Thus, the apparatus illustrated in FIG. 11 can be conveniently used to monitor all body activities of a person during a sleep session, after which the memory unit 304 could be removed and its contents later analyzed for any of the above-described body activities.

Figure 12:
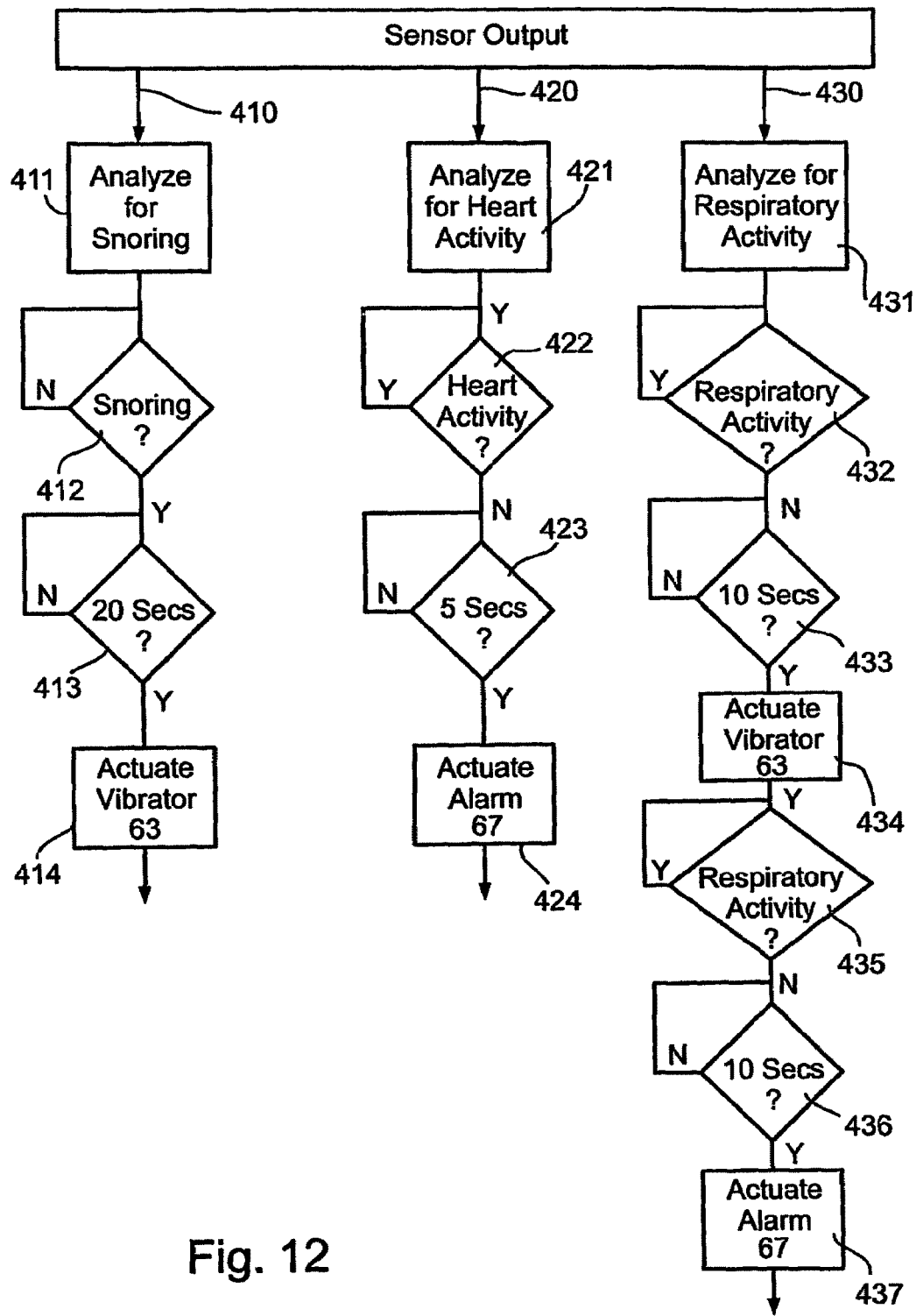
FIG. 12 is a flowchart illustrating the overall operation of the apparatus of FIG. 5 or of FIG. 11.

FIG. 12 is a flowchart illustrating an example of the above-described operation of the processor control system 64 (FIG. 5) or 302 (FIG. 11). In this example, the output from sensor assembly 10 is processed in three separate processing channels: channel 410 analyzes the sensor output for snoring and controls vibrator 63; channel 420 analyzes the sensor output for heart activity and controls alarm 67; and channel 430 analyzes the sensor output for respiratory activity and controls both vibrator 63 and alarm 67.

Thus, as shown in FIG. 12, in the snore-analysis channel 410, the processor analyzes the output signal from sensor assembly 10 for snoring (block 411); if a snoring condition is detected (block 412), and persists for 20 seconds (block 413), vibrator 63 is actuated to produce a response which tends to interrupt the snoring, and thereby to reduce or eliminate the snoring.

In heart-activity channel 420, the output signal from sensor assembly 10 is analyzed for heart activity (block 421), and if no heart activity is sensed for a period of 5 second (blocks 422, 423), alarm 67 is actuated. Alarm 67 may be located at the monitoring site so that others in the vicinity, e.g. a bed partner, will be alerted to the alarm condition. An alarm may also be at a remote location, e.g. a crisis center, to alert those at the remote location as to the alarm condition.

In respiratory-activity channel 430, the output signal from sensor assembly 10 is analyzed to determine whether a cessation of breathing has occurred (block 431). When this occurs (block 432), and persists for 10 seconds (block 433), vibrator 63 is actuated (block 434) in an attempt to restart the breathing. However; if the cessation of breathing continues for an additional 10 seconds (block 435), alarm 67 is then actuated (block 436) to alert one in the immediate vicinity and/or at a remote location as to the alarm condition.

The analysis of the output signal from sensor assembly 10 in each of the channels 410, 420, 430, is based on the frequency components of the sensor output signal corresponding to the physiological phenomenon to be sensed in the respective channel. For example, the components of the sensor signal corresponding to snoring activity fall mainly within the bandwidth of 30-120 Hz, more particularly within the bandwidth of 35-85 Hz; the components corresponding to heart activity fall mainly within the bandwidth of up to 5 Hz; and the components corresponding to respiratory activity fall mainly within the bandwidth of up to 0.3 Hz.

Figure 13:
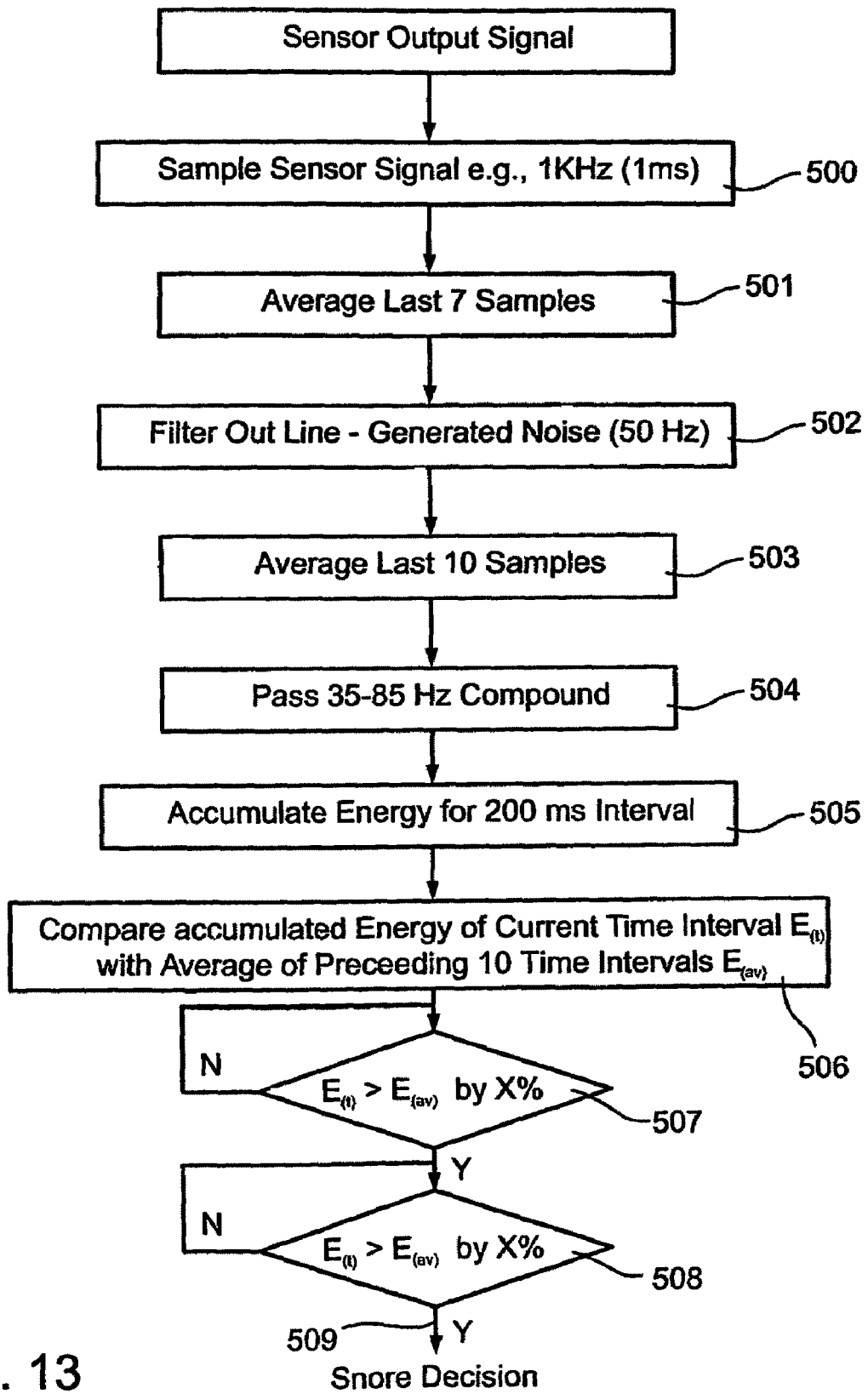
FIG. 13 is a flowchart particularly illustrating an example of the operation of the apparatus of FIG. 5 or FIG. 11 for controlling a stimulus device to reduce or eliminate snoring by a "stimulus and response" reflex process.

FIG. 13 is a flowchart illustrating an example of the analysis in the snore-activity channel 410 to determine whether a snoring condition exists, and to actuate vibrator 63 (or other stimulus device) in response to the detection of such condition, in order to reduce or eliminate snoring by the above-described "stimulus and response" reflex process. A similar analysis may be made in the heart-activity channel 420, and in the respiratory-activity channel 430, with respect to the frequency components of the frequency band corresponding to the respective physiological phenomenon to be detected.

Thus, as shown in FIG. 13, the output signal from sensor 10, which is analyzed in the snore-activity processing channel 410 of FIG. 12, is sampled at a frequency of 1 KHz i.e., 1 ms (block 500), and a plurality (e.g. 7) samples are averaged (block 501). The average is then passed through a 50 Hz notch filter to remove supply-line generated artifacts (block 502), and another average is taken of another plurality of samples, e.g. 10 samples (block 503).

The resultant smoothed signal is then passed through a filter to filter out the frequency components of the sensor signal within the bandwidth of the physiological phenomenon to be detected, in this case the presence of snoring. The snoring components of the sensor signal are mostly within the band of 30-120 Hz, more particularly within the band of 35-85 Hz. The latter frequency components are detected (block 504), and the absolute value of the energy (i.e., the energy of both polarities) is accumulated over a preselected time interval, e.g. 200 ms (block 505). The so-accumulated energy of the current time interval E(t), is compared with the average of such energy accumulated during a plurality (e.g. 10) of the preceding predetermined time intervals E(av), to determine whether the accumulated energy in the respective time interval E(t) exceeds such average E(av) by at least a predetermined percentage (X %). If so, this would indicate that the current sample represents the start of a snore condition.

However, a snore condition is not determined to be present until two successive comparisons indicate a snore condition (blocks 507, 508). When this occurs, vibrator 63 is actuated to produce a stimulus for invoking a response tending to produce an interruption in the sleeping of the person, and thereby to reduce or eliminate the snoring condition by the above-described "stimulus and response" reflex process. Vibrator 63 is deactivated immediately when the analysis of the sensor output signal indicates the snore condition has ceased.

The predetermined percentage (X %) of blocks 507 and 508 determines the sensitivity of the apparatus before actuating the vibrator. Preferably, the apparatus includes a manual selector control, as represented by manual selectors 306 in FIG. 11, permitting this sensitivity to be manually varied according to the prevailing conditions. For example, X % in blocks 507 and 508 of FIG. 13 could be within the range of 50-100%, preferably about 60-70%.

The time period during which the sensor signal is accumulated (block 505) determines the time periods at which the above comparisons are made, and therefore, the resolution of the system. The time period should be substantially less than the inhalation and exhalation half-cycle times of the person's respiration cycle such that the feedback response produced by the activation of the vibrator is time-coordinated to the actual snoring as sensed by the system during the person's respiration cycle. Thus, in this example, it is desired to initiate the vibrator action immediately upon sensing a snoring condition, and to terminate the vibrator action immediately upon sensing the cessation of snoring, such that the reflex response, produced by activation of the vibrator, will accompany as much as possible the snoring condition to be reduced or eliminated.

Utilizing a mechanical vibration sensor to detect snoring, as described above, provides a number of important advantages over known technique utilizing a microphone or the like for detecting the snoring sounds. Thus, by directly sensing and analyzing mechanical vibrations in an external part of the person's body, the apparatus is less sensitive to external sounds than in a sound-detector type sensor. Moreover, since the parameter being sensed is not the sound itself, but rather the condition (vibrations) producing the sound, the stimulus applied to the person for reducing or eliminating the snoring can be much more closely time-coordinated to the snoring. A further important advantage in the described sensor and apparatus is that the same apparatus can also be used for detecting many other conditions, e.g. apnea, heart failure, body movements, comfortable arousal times for a wake-up call, etc.

Figure 14:
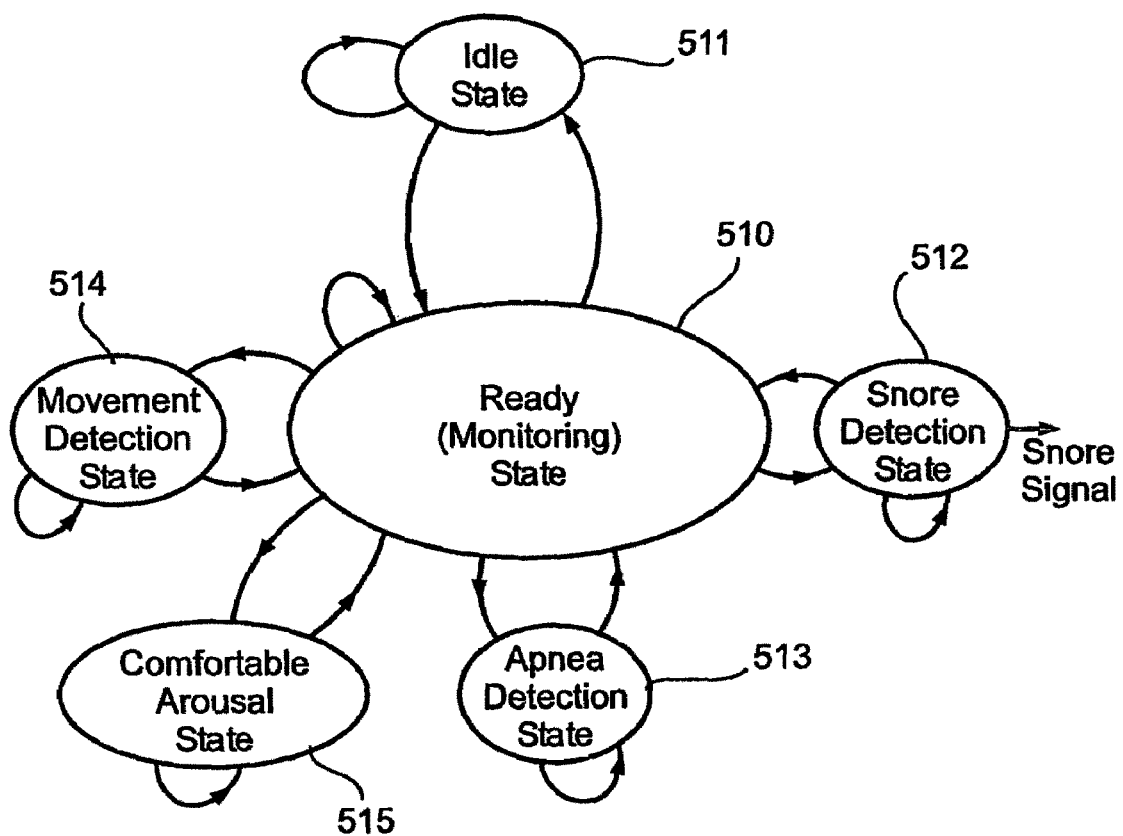
FIG. 14 is a Machine State diagram illustrating another operation of the sensor apparatus in accordance with the present invention.

FIG. 14 is a State Machine diagram illustrating the described apparatus programmed to detect a number of different states. In the diagram of FIG. 14, the system is normally in the Monitoring (or Ready) State 510 which it assumes from the Idle State 511 as soon the monitored person occupies the bed and/or actuates the On-button. While in this State the output from the vibration sensor is continuously monitored. If a snore condition is detected, the system goes to the Snore State 512; if an apnea condition is detected, the system goes to the Apnea State 513; if significant body movements are detected, e.g. by position changes or RLS (restless leg syndrome), the system goes to the Movement State 514; and where the system detects a comfortable arousal time, (e.g. immediately following an REM sleep state) during a preselected arousal time period, the system goes to the Comfortable Arousal State 515.

As one example, the system could be operated as follows: where the system is in the Snore Detection State 512, the above-described stimulus device (e.g. vibrator 63) could be activated to thereby produce the response for reducing or eliminating snoring according to the above-described "stimulus and response" reflex process. Preferably, however, if movement is detected such that the apparatus goes to the Movement Detection State 514, the stimulus device would be disabled, since such body movements would completely mask the mechanical vibrations signal indicating a snoring condition. Whenever apnea is detected, the alarm 67 could be actuated as described above. If a wake-up alarm time has been preselected, the wake-up alarm would be actuated only if the Comfortable Arousal State 515 is detected. The wake-up alarm could be in the form of a separate wake-up alarm device, or a more intense powering of the stimulus device (vibrator 63).

Figure 15:
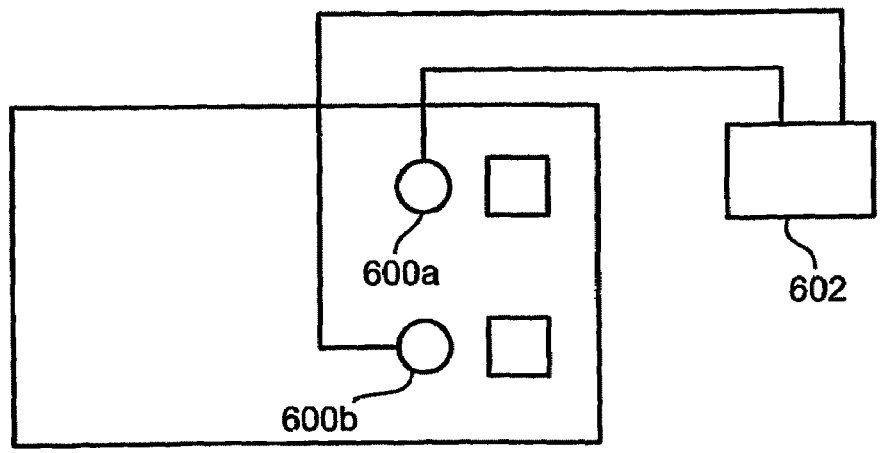
FIG. 15 illustrates sensor apparatus including two sensor assemblies for use by two persons occupying a common bed in order to reduce or eliminate snoring by one or both persons.

FIG. 15 illustrates the invention embodied in apparatus including two sensor assemblies for use by two persons occupying a common double bed. Such apparatus can be used, for example, to eliminate or reduce snoring by one or both persons, to alert one of an emergency condition occurring in the other, or to control a wake-up alarm by one or both persons so as to be actuated at a comfortable wake-up period for the respective person.

The apparatus illustrated in FIG. 15 includes two sensor assemblies 600a, 600b, connected together through a common electronic unit 602. For example, the common electronic unit 602 may be incorporated in one of the sensor assemblies to which the other sensor assembly is electrically connected by electrical leads, wireless, etc.

Figure 16:
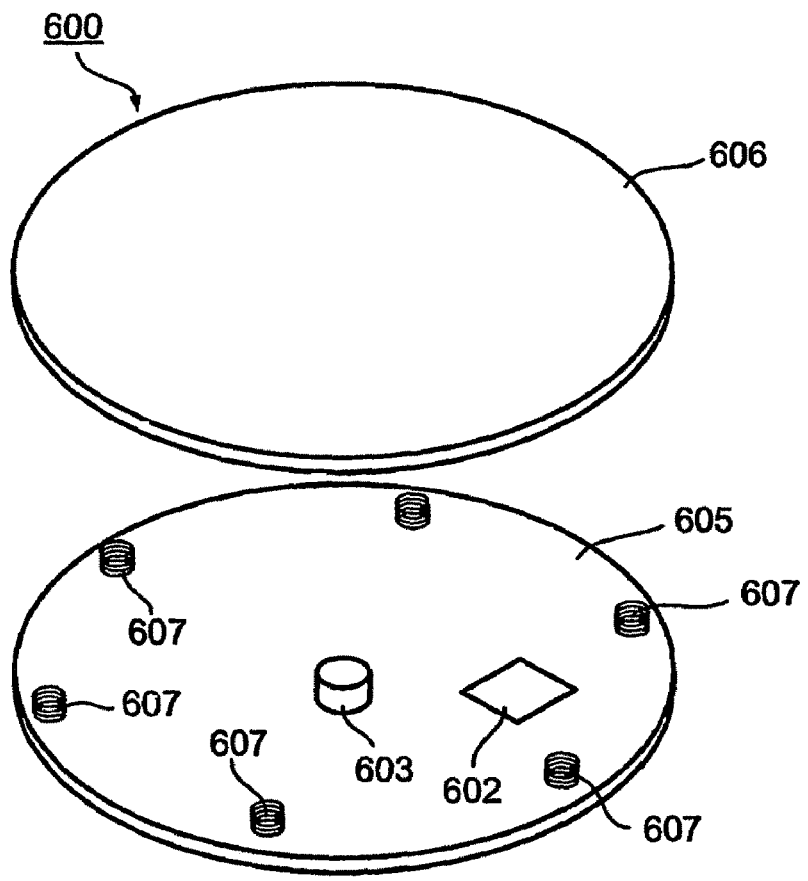
FIG. 16 is an exploded view illustrating one sensor assembly in the apparatus of FIG. 15.
Figure 17:
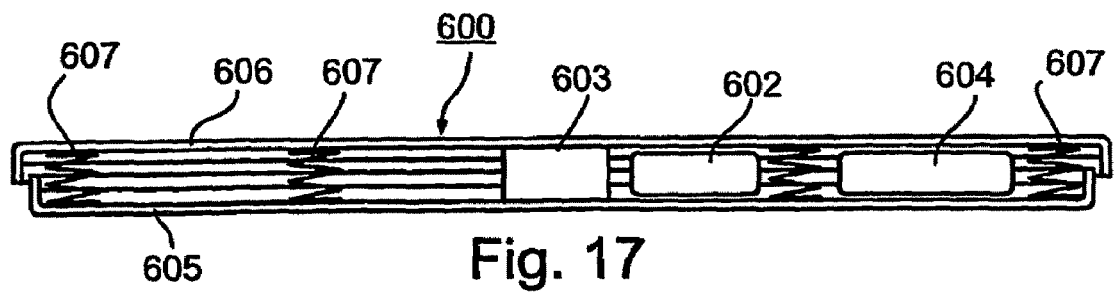
FIG. 17 is a transverse sectional view of the sensor assembly of FIG. 16.

FIGS. 16 and 17 illustrate the construction of one of the sensor assemblies, therein designated 600. It includes, in addition to the electronic unit 602, a sensor unit 603 which may be of any of the above-described constructions, e.g. sensor unit 10 of FIGS. 1 and 2. The electronic unit 602 could also be of any of the above-described constructions, except modified to accommodate sensor output signals from the two sensors of the two assemblies 600a, 600b. In this application of the invention, the stimulus device, corresponding to vibrator 63, is a separate unit and is not included within the sensor assembly.

All the foregoing elements of the sensor assembly are sandwiched between two circular plates 605, 606 and are circumscribed by a plurality of coiled springs 607. Preferably, sensor unit 603 is located centrally of the circular plates 605, 606, and the coiled springs 607 are located around the periphery of the circular plates. The two circular plates 605, 606 may be, for example, 200 mm in diameter.

Figure 18:
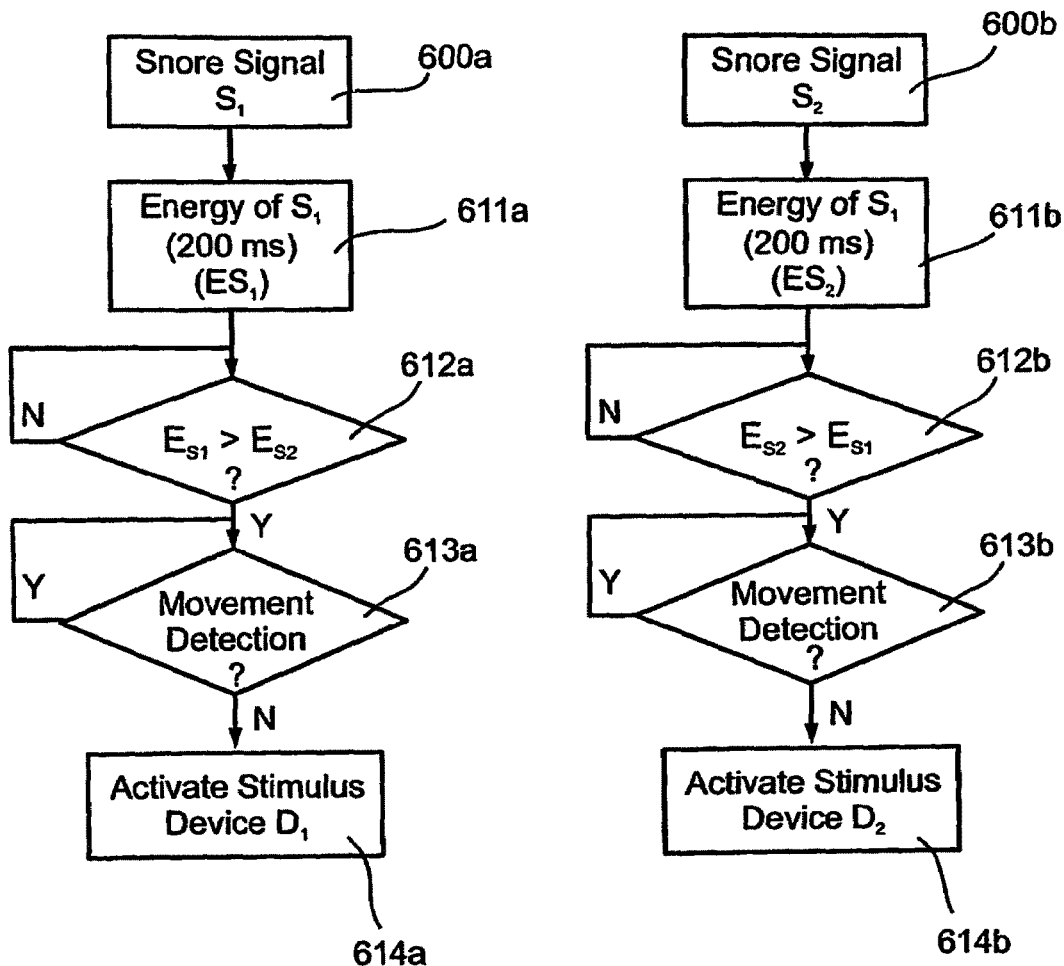
FIG. 18 is a flowchart illustrating an example of the operation of the two-sensor apparatus of FIG. 15.

FIG. 18 is a flowchart illustrating a typical operation wherein the apparatus of FIGS. 15-17 is used to reduce or eliminate snoring by each of the two occupants of the bed. In such cases a stimulus device, such as a vibrator, would be provided for and adjacent to each user to produce the response in the above-described "stimulus and response" reflex process for reducing or eliminating snoring, or for otherwise producing better quality sleeping.

Thus, electronic unit 602 processes the signals outputted by the sensor unit 603 of the two sensor assemblies 600a, 600b. When a snoring condition is sensed in either sensor output signal, as described above and as shown by the Snore Detection State 512 of the Machine State diagram in FIG. 14, the energy of such a snore signal ($S_1$ $S_2$) is accumulated for a predetermined time interval, e.g. 200 ms (blocks 611a, 611b). A comparison is then made as to which snore signal is more intense (blocks 612a, 612b). The snore signal which is more intense results in the activation of the respective stimulus device, but only if large body movements are not detected by the respective occupant (movement detection state 514, FIG. 14), as shown by blocks 613a, 613b, 614a and 614b of FIG. 18.

In some cases, it may be desirable to have only one stimulus device for only one of the occupants. In such case, the other sensor assembly could still be used without a stimulus device so that its sensor output would be used merely as a basis for comparing the other output signal in the snore determination decision.

Another possible application of the invention would be to use both sensor assemblies for detecting snoring by one person. In such an application, one sensor assembly 600a would be located to underlie one body part, such as the chest, producing more intense mechanical vibrations upon the occurrence of snoring by the person than another body part, such as the legs. In such an application of the invention, the output of the sensor underlying to the occupant's legs could be used for sensing and cancelling-out noise signals not generated by the snore condition of the person.

It will be appreciated that the sensors in the above-described embodiments can be placed on or under the mattress, in between two mattresses, under a pillow, or the like. It will be further appreciated that the stimulus device need not be a vibrator, but could be another type of stimulus device, such as a sound device, a light device, a body displacement device, and the like, tending to reduce or eliminate snoring by the above-described "stimulus and response" reflex process. Also, while the preferred embodiments described above utilize specific constructions of vibration sensors, other types of sensors, e.g. optical sensors, could be used for sensing the vibrations. While specific physiological phenomena are described as being detected by the novel sensors, such sensors could detect other physiological phenomena, such as asthma, oxygen saturation, etc., for example, by analyzing the respiratory and cardiac activity.

Accordingly, while the invention has been described with respect to several preferred embodiments, it will be appreciated that these are set forth merely for purposes of example, and that many other variations, modifications and applications of the invention may be made.

What is claimed is:

1. Apparatus for controlling snoring or other predetermined body condition by a person, comprising: a sensor for sensing said predetermined body condition of the person while sleeping; and for outputting a sensor signal corresponding to the sensed condition; a stimulus device effective, when actuated, to immediately produce a response in the person tending to interrupt said sensed body condition; and a processor for processing said outputted sensor signal to determine whether it indicates the presence of said sensed body condition, and if so, for actuating said stimulus device to produce said response tending to interrupt said sensed body condition;
   characterized in that said sensor is a mechanical vibrations sensor and is included between, and in contact with, a pair of plates of larger size than said sensor for sensing mechanical vibrations in an external part of the person's body and for transmitting said mechanical vibrations to said sensor for generating and outputting said sensor signal.

2. The apparatus according to claim 1, wherein said processor:
   analyzes said sensor signal for frequency components within a predetermined frequency band;
   accumulates the energy of the sensor signal within said predetermined frequency band for a preselected time interval;
   compares said accumulated energy for each predetermined time interval with the average of the accumulated energy in a plurality of the preceding preselected time intervals; and controls the actuation of said stimulus device as a result of such comparison.

3. The apparatus according to claim 2, wherein said processor controls the actuation of said stimulus device in accordance with a determination of whether or not the accumulated energy in the preselected time interval exceeds by a predetermined percentage the average of the accumulated energy in said plurality of preceding preselected time intervals.

4. The apparatus according to claim 3, wherein said processor actuates said stimulus device when the accumulated energy in each of at least two successive preselected time intervals exceeds by said predetermined percentage the average of the accumulated energy in the plurality of preceding preselected time intervals.

5. The apparatus according to claim 3, wherein said apparatus includes a manual control for varying said predetermined percentage, and thereby for varying the sensitivity of the apparatus.

6. The apparatus according to claim 1, wherein said preselected time interval is substantially less than the inhale and exhale half-cycle times of the person's respiration cycle time such that the actuation of the stimulus device is closely time-coordinated with the sensed body condition during the person's respiration cycle.

7. The apparatus according to claim 1, wherein said sensor senses said mechanical vibrations in the part of the person's body by causing said mechanical vibrations sensor to change the transit time of an acoustic wave transmitted from a transmitter to a receiver in an acoustic channel, and by producing a measure of said changes of transit time.

8. The apparatus according to claim 1, wherein said predetermined body condition is a snoring condition and wherein said apparatus comprises two of said mechanical vibration sensors for sending mechanical vibrations in two different external body parts, and for outputting sensor signals corresponding to the vibrations sensed by each sensor; said processor processing both said outputted sensor signals to determine whether they indicate a snoring condition exists.

9. The apparatus according to claim 8,
wherein said two mechanical vibration sensors are coupled together for sensing mechanical vibrations in different external body parts of the same person, one body part producing more intense mechanical vibrations upon the occurrence of snoring by the person than the other body part;
wherein said apparatus includes a stimulus device;
and wherein said processor processes both said outputted sensor signals to determine whether they indicate a snoring condition exists in said person, and upon such a determination, actuates said stimulus device to produce said response tending to interrupt the snoring by the person.

10. The apparatus according to claim 1, wherein said processor further processes said outputted sensor signal to determine whether relatively large body movements are occurring in a part of said person's body, and if so, to disable actuation of the stimulus device during the occurrence of such relatively large body movements.

* * * * *